Jan. 15, 1963 V. APKARIAN Plant Pat. 2,217
GRAPE VINE
Filed Jan. 8, 1962
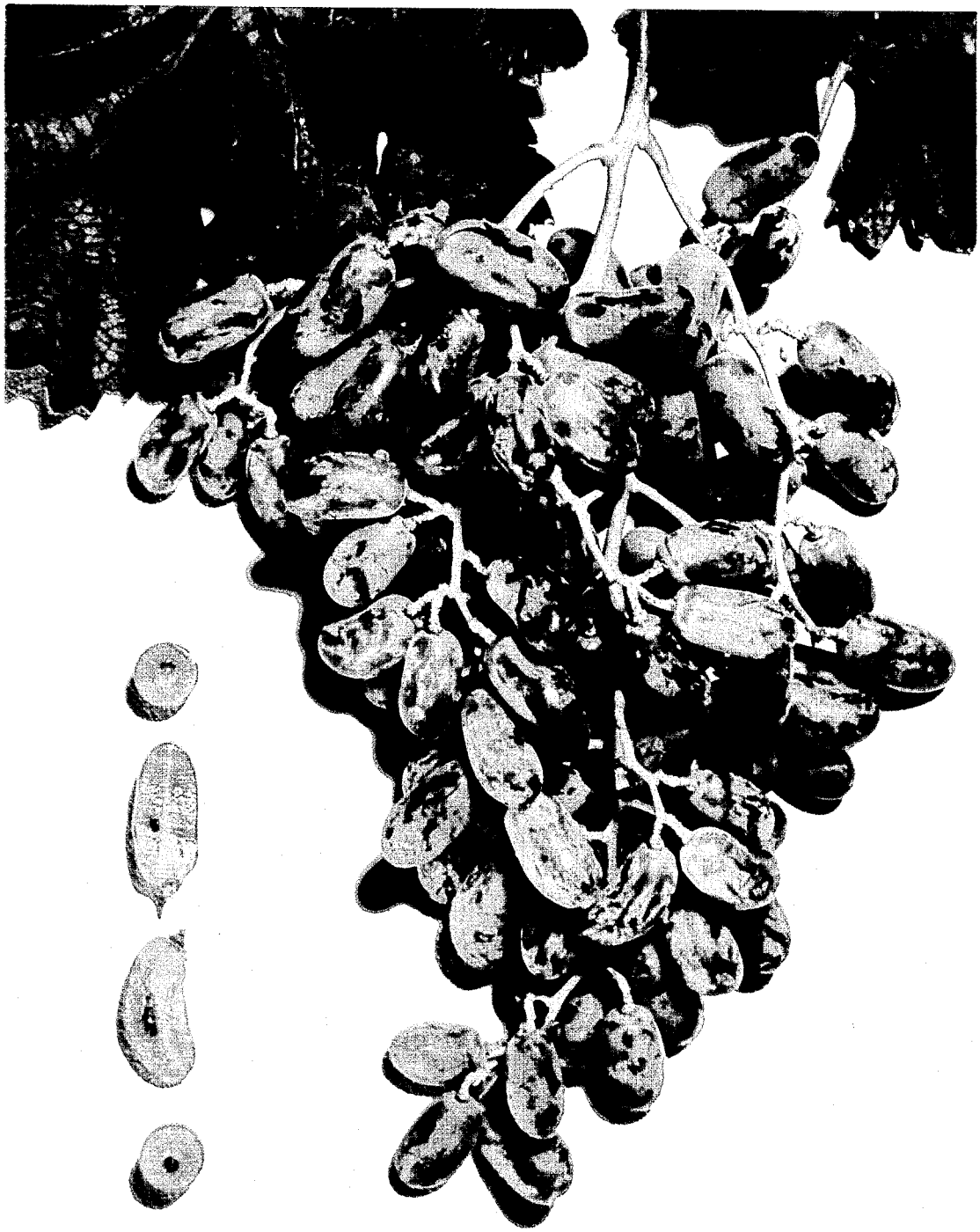
VAHAN APKARIAN
INVENTOR
HUEBNER & WORREL
ATTORNEYS
BY
Richard M. Worrel United States Patent Office Plant Pat. 2,217
Patented Jan. 15, 1963

2,217
GRAPE VINE

Vahan Apkarian, 20682 E. Manning Ave., Reedley, Calif.

Filed Jan. 8, 1962, Ser. No. 165,053
1 Claim. (Cl. 47—62)

The present invention relates to a new and distinct variety of grape vine.

The new variety of grape vine originated in a vineyard of Emperor (unpatented) grape vines maintained by the applicant at 20500 East Manning Avenue, Reedley, California. The climatic conditions existing in the subject vineyard are comparable to those enjoyed by the San Joaquin Valley of central California, and include a mild winter of light rainfall (approximately ten inches) and a hot, dry summer. During the maintenance of said vineyard, the new variety was recognized as a chance variation, or mutation, growing on an Emperor vine, which it most nearly resembles. However, among other features, the fruit of the discovered variety can readily be distinguished from that of the Emperor by its unusual configuration. In general appearance, the berries borne by the variety of the present invention are of the shape of a kidney-bean, being nearly identical in configuration to commercially available candy jelly-beans, albeit considerably larger.

When originally recognized as a chance variation of an Emperor vine, it was noticed that the new variety bore fruit which ripened about two weeks ahead of the Emperor and had markedly superior coloring characteristics in that each berry readily achieved purplish-red coloring over the major portion of its skin, except for a small area of light green at its base. Other distinctive features observed were a firm, crisp berry flesh, of delicate pink coloring and sweet flavor, a smooth, strong skin which resisted puncturing, a tough leathery stem, and firmly set cap stems. The latter characteristic is so pronounced that an entire bunch of ripened berries can be lifted by a single berry without loosening its cap stem. A preponderance of the berries have a single seed which is eccentrically located and tends to cause the berries to assume a longitudinally arcuate form.

After having discovered the new variety as a chance variation of an Emperor, the grape vine of the present invention was asexually reproduced by cuttings at 20500 East Manning Avenue, Reedley, California, under the direction and control of the applicant. The cuttings grew well and exhibited vigorous and healthy qualities of growth. The fruit subsequently borne by vines grown from such cuttings had the same early ripening and other distinctive characteristics observed in the fruit of the originally discovered chance variation. The unusual berry configuration of "jelly-bean" form is typical of the fruit borne by the vines of the subject variety.

The accompanying drawing, reproduced from a color photograph, shows leaves from a vine of the new variety along with a typical specimen of a bunch of grapes borne by the subject grape vine. Also shown are portions of individual berries which have been cut along various transverse and horizontal planes to illustrate the "jelly-bean" berry configuration, flesh coloring, and single seed location occurring in most berries.

The following is a detailed description of the pomological characteristics of the subject grape vine. Color terminology is in accordance with that of the "Dictionary of Color," Maerz and Paul, second edition.

Where dimensions, sizes, colors and other characteristics are given, it is to be understood that such characteristics are approximations of averages set forth as accurately as practicable.

Vine: The vine is similar in characteristics to that of the Emperor grape vine.

*Size.*—Medium large.
*Growth.*—Vigorous.
*Productivity.*—Medium and regular.
*Canes.*—Medium to large. Joints—average spacing. Tendrils—medium slender, medium short, abundant, and medium delicate. Color—medium to light green (20–F–6).

Foliage:

*Leaves.*—Number — average. Color — dark green (23–L–10) with irregular patches of light green (20–F–6).

Flowers:

*Number.*—Average. *Length of blooming season.*—Fourteen days.
*Date of bloom.*—May 10.
*Blossom color.*—Light green (17–G–3) varying in relation to maturity.
*Shape and size of cluster.*—Narrow and tapering, long, medium.
*Average length of peduncle.*—2".
*Reproduction organs.* — Stamens — medium. Filaments—long. Pollen—normal.

Fruit:

*Maturity.*—Approximate dates—begins about September 1–10, and normally can be picked from September 1 to October 15 for shipping. In extreme situations, the picking can be delayed until November without shattering of individual bunches. This is due to the unusual strength and tenacity of the berry cap stem. Two weeks before the Emperor grapes.
*Size of berry.*—Large.
*Diameter.*—17 millimeters.
*Base to apex.*—25 millimeters.
*Average number of clusters to vine.*—22.
*Average number of berries to cluster.*—125, berries unusually uniform and spaced.
*Number of seeds to berry.*—Usually 1 but rarely 2; usually only one and on only one side of each berry.
*Productivity.*—Comparable to Emperor.
*Stem brush.*—About ½" in length and firmly set.
*Skin.*—Tight.
*Color.*—Skin of purplish-red (55–L–8) over major portion of berry to a small basal area of light green (20–E–3). Flesh is a delicate light pink (1–B–8) except for a very small basal portion of light green (20–E–3).
*Ripening.*—Begins—August 15. Peak — September 5. End—September 15.
*Clusters ripen.*—Evenly — much more evenly than Emperor.
*Texture.*—Medium.
*Flavor.*—Sweet.
*Aroma.*—Delicate, not pronounced.
*Eating quality.*—Excellent.
*Juice quality.*—Medium.
*Shipping quality.*—Excellent.
*Storing quality.*—Exceptionally good, and a marked improvement over Emperor.
*Uses.*—Primarily fresh table; secondarily wine.

Most unusual characteristics: Form—configuration of a kidney-bean, or, more nearly, of the shape of commercially available candy jelly-beans.

The new variety grape vine has been described as it exists under the ecological conditions prevailing in the central San Joaquin Valley of California. Normal variations can be expected under different environmental conditions.

Having thus described my instant grape vine, I claim:

A new and distinct variety of grape vine, substantially as illustrated and described, characterized principally by its bearing of fruit of the well-known shape of candy jelly-beans, the fruit maturing approximately two weeks earlier than the Emperor grape (unpatented), which it most nearly resembles, but from which it is distinguished by its jelly-bean configuration, its purplish-red color over a major portion of its skin, its firm, crisp, sweet flesh of a light pink color, and by a preponderance of its berries each having only a single eccentrically located seed.

No references cited.